(12) United States Patent
Dargazanli et al.

(10) Patent No.: US 7,750,025 B2
(45) Date of Patent: *Jul. 6, 2010

(54) DERIVATIVES OF N-PHENYL (PIPERIDINE-2-YL) METHYL BENZAMIDE, PREPARATION METHOD THEREOF AND APPLICATIONS OF SAME IN THERAPEUTICS

(75) Inventors: Gihad Dargazanli, Cachan (FR); Genevieve Estenne-Bouhtou, Chevilly-Larue (FR); Pascale Magat, Chilly Mazarin (FR)

(73) Assignee: sanofi-aventis, Paris (FR)

( * ) Notice: Subject to any disclaimer, the term of this patent is extended or adjusted under 35 U.S.C. 154(b) by 876 days.

This patent is subject to a terminal disclaimer.

(21) Appl. No.: 11/405,169

(22) Filed: Apr. 17, 2006

(65) Prior Publication Data

US 2006/0223885 A1    Oct. 5, 2006

Related U.S. Application Data

(63) Continuation of application No. PCT/FR2004/002640, filed on Oct. 15, 2004.

(30) Foreign Application Priority Data

Oct. 17, 2003 (FR) .................................. 03 12140

(51) Int. Cl.
*A61K 31/445* (2006.01)
*C07D 409/12* (2006.01)

(52) U.S. Cl. .................. 514/324; 514/241; 514/256; 514/307; 514/311; 514/318; 514/321; 514/326; 546/201; 546/202; 546/212

(58) Field of Classification Search ............ 514/241, 514/249, 256, 307, 311, 318, 321, 322, 324, 514/326; 546/113, 114, 115, 139, 152, 194, 546/198, 199, 201, 205, 209, 210, 211, 212, 546/214; 544/212, 288, 333, 349, 353
See application file for complete search history.

(56) References Cited

U.S. PATENT DOCUMENTS

| | | | |
|---|---|---|---|
| 2,928,835 A | | 3/1960 | Jacob et al. |
| 3,336,300 A | | 8/1967 | Santilli et al. |
| 5,254,569 A | | 10/1993 | Cheeseman et al. |
| 7,205,319 B2 * | | 4/2007 | Dargazanli et al. ......... 514/331 |
| 7,226,917 B2 | | 6/2007 | Dargazanli et al. |
| 7,288,656 B2 | | 10/2007 | Dargazanli et al. |
| 7,335,670 B2 * | | 2/2008 | Dargazanli et al. ......... 514/318 |
| 2006/0223861 A1 | | 10/2006 | Dargazanli et al. |
| 2007/0208006 A1 | | 9/2007 | Dargazanli et al. |
| 2008/0070941 A1 | | 3/2008 | Dargazanli et al. |

FOREIGN PATENT DOCUMENTS

| EP | 0 366 006 | 10/1989 |
|---|---|---|
| EP | 0 365 030 | 4/1990 |
| EP | 0499995 | 8/1992 |
| WO | WO 92/12128 | 7/1992 |
| WO | WO 03/089411 | 10/2003 |

OTHER PUBLICATIONS

Harsing et al. "Glycine transporter type-1 and its inhibitos" Current Medi. Chem. v.13, p. 1017-1044 (2006).*
Sur et al. "Glycine transporter 1 inhibitoers ... " Current Drug targets v.8, p. 643-649 (2007).*
Dutta et al. "Potent and selective ligand ... " J. Med. chem. v.41 (5), p. 699-705 (1998).*
Wermuth "The practice of medicinal chemistry" p. 203-207 (1996).*
Froelich, O., et. al., Asymmetric Synthesis. 39.1 Synthesis of 2-(1-Aminoalkyl)piperidines via 2-Cyano-6-phenyl Oxazolopiperidine , Journal of Organic Chemistry, American Chemical Society vol. 61, (1996) pp. 6700-6705.
U.S. Appl. No. 12/402,276, filed Mar. 19, 2009, Dargazanli et al.

(Continued)

*Primary Examiner*—Celia Chang
(74) *Attorney, Agent, or Firm*—Kelly L. Bender

(57) ABSTRACT

Compounds of formula (I) as defined herein:

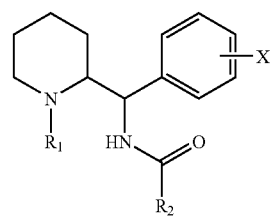

are useful for treating behavioral disorders associated with dementia, psychoses, in particular schizophrenia (deficient form and productive form) and acute or chronic extrapyramidal symptoms induced by neuroleptics; for the treatment of various forms of anxiety, panic attacks, phobias, and compulsive obsessive disorders; for treating various forms of depression, including psychotic depression; for treating disorders caused by alcohol abuse or weaning from alcohol, sexual behavior disorders, eating disorders and for treating migraine. Moreover, the compounds of the invention may be used for treating painful muscle contracture in rheumatology and in acute spinal pathology; for treating spastic contractures of medullary or cerebral origin; for the symptomatic treatment of acute and subacute pain of light to moderate intensity; for treating intense and/or chronic pain, neurogenic pain and intractable pain; for treating Parkinson's disease and Parkinson-like symptoms of neurodegenerative origin or induced by neuroleptics; for treating partial primary and secondary generalized epilepsy of simple or complex symptomology, mixed forms and other epileptic syndromes in addition to another antiepileptic treatment, or in monotherapy, for the treatment of sleep apnea, and for neuroprotection.

4 Claims, No Drawings

OTHER PUBLICATIONS

Balboni et al, Synthesis and activity of 3-pyridylamine ligands at central nicotinic receptors, Eur. J. Med. Chem., 2000 (35) pp. 979-988.

Javitt et al, Reversal of Phencyclidine-Induced Effects by Glycine and Glycine Transport Inhibitors, Biol. Psychiatry, 1999 (45) pp. 668-679.

Jeong et al, A New Method for the Preparation of Perfluoroalkylated Triphenylethylene Derivatives, Tetrahedron Letters, 1996 (37) 33, pp. 5905-5908.

Niemers et al, Pyridylalkyl-substiuierte Amine, Communications, Sep. 1976, pp. 593-595.

Shimada et al, Synthesis and Gastric Antisecretory Activity of N-cyano-N'-(phenyl-pyridinaylmethyl)guanidine Derivatives, Chem. Pharmn. Bull., 1984 (32)12 pp. 4893-4906.

Thai et al, Asymmetric Synthesis and Pharmacology of Methylphenidate and Its Para-Substituted Derivatives, J. Med. Chem., 1998 (41) pp. 491-601.

* cited by examiner

DERIVATIVES OF N-PHENYL (PIPERIDINE-2-YL) METHYL BENZAMIDE, PREPARATION METHOD THEREOF AND APPLICATIONS OF SAME IN THERAPEUTICS

CROSS-REFERENCE TO RELATED APPLICATIONS

This application is a continuation of PCT/FR2004/002640, filed Oct. 15, 2004, which claims priority from French Patent Application No. 0312140, filed Oct. 17, 2003.

SUMMARY OF THE INVENTION

The compounds of the invention correspond to the general formula (I)

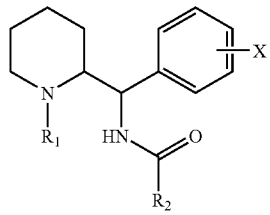

in which $R_1$ represents either a hydrogen atom or a linear or branched $(C_1-C_7)$alkyl group optionally substituted with one or more fluorine atoms, or a $(C_3-C_7)$cycloalkyl group, or a $(C_3-C_7)$cycloalkyl$(C_1-C_3)$alkyl group, or a phenyl$(C_1-C_3)$alkyl group optionally substituted with one or two methoxy groups, or a $(C_2-C_4)$alkenyl or $(C_2-C_4)$alkynyl group, X represents a hydrogen atom or one or more substituents chosen from halogen atoms and trifluoromethyl and linear or branched $(C_1-C_4)$alkyl and $(C_1-C_4)$alkoxy groups, $R_2$ represents a group chosen from naphthyl, pyridinyl, pyrimidinyl, pyrazinyl, pyridyl, triazinyl, indanyl, indenyl, quinolyl, isoquinolyl, quinazolyl, quinoxalyl, phthalazinyl, thienyl, furyl, pyrrolyl, imidazolyl, pyrazolyl, oxazolyl, thiazolyl, isoxazolyl, isothiazolyl, thiadiazolyl, oxadiazolyl, triazolyl, benzothienyl, benzofuryl, benzimidazolyl, benzothiazolyl, indolyl, isoindolyl, indazolyl, benzoxazolyl, benzisoxazolyl, benzotriazolyl, benzisothiazolyl, dihydroindolyl, pyrrolopyridyl, furopyridyl, thienopyridyl, imidazopyridyl, oxazolopyridyl, thiazolopyridyl, pyrazolopyridyl, isoxazolopyridyl, isothiazolopyridyl, tetrahydroquinolyl and tetrahydroisoquinolyl groups, and optionally substituted with one or more substituents chosen from halogen atoms and $(C_1-C_4)$alkyl, $(C_1-C_4)$alkoxy, thio$(C_1-C_4)$alkyl or phenyl groups optionally substituted with one or more substituents chosen from halogen atoms and trifluoromethyl, $(C_1-C_4)$ alkyl and $(C_1-C_4)$alkoxy groups.

The compounds of general formula (I) may exist in the form of the threo racemate (1R,2R;1S,2S) or in the form of enantiomers (1R,2R) or (1S,2S); they may exist in the form of free bases or of acid-addition salts.

BACKGROUND OF THE INVENTION

Compounds of structure similar to that of the compounds of the invention are described in patent U.S. Pat. No. 5,254,569 as analgesics, diuretics, anticonvulsivants, anesthetics, sedatives and cerebroprotective agents, via a mechanism of action on the opiate receptors. Other compounds of similar structure are described in patent application EP-0 499 995 as 5-$HT_3$ antagonists that are useful in the treatment of psychotic disorders, neurological diseases, gastric symptoms, nausea and vomiting.

DETAILED DESCRIPTION OF THE INVENTION

The preferred compounds of the invention lack activity on the opiate or 5-$HT_3$ receptors and show particular activity as specific inhibitors of the glycine transporters glyt1 and/or glyt2.

The compounds of general formula (I) in which $R_1$ is other than a hydrogen atom may be prepared via a process illustrated by Scheme 1 below.

Coupling of a diamine of general formula (II), in which $R_1$ and X are as defined above (with $R_1$ other than a hydrogen atom) with an activated acid or an acid chloride of general formula (III) in which Y represents an activated OH group or a chlorine atom and $R_2$ is as defined above, is performed using the methods known to those skilled in the art.

Scheme 1

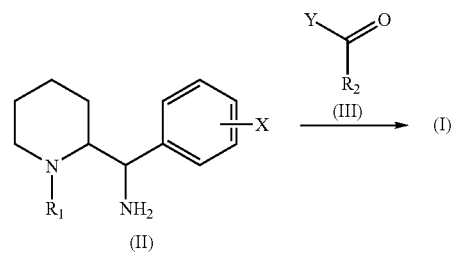

The diamine of general formula (II) may be prepared via a process illustrated by Scheme 2 below.

Scheme 2

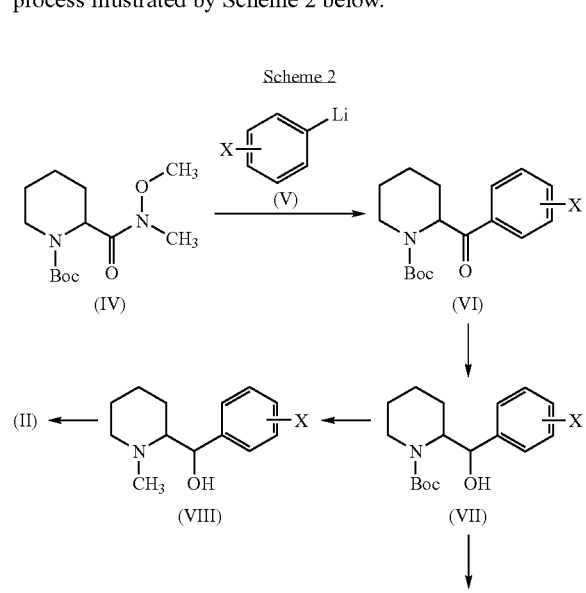

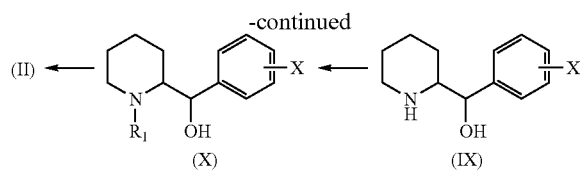

The Weinreb amide of formula (IV) is reacted with the phenyllithium derivative of general formula (V), in which X is as defined above, in an ether solvent such as diethyl ether, between −30° C. and room temperature; a ketone of general formula (VI) is obtained, which is reduced to the alcohol of threo configuration of general formula (VII) with a reducing agent such as K-Selectride® or L-Selectride® (potassium or lithium tri-sec-butylborohydride), in an ether solvent such as tetrahydrofuran, between −78° C. and room temperature. The carbamate of general formula (VII) may then be reduced to threo N-methylamino alcohol of general formula (VIII) via the action of a mixed hydride such as lithium aluminum hydride, in an ether solvent such as tetrahydrofuran, between room temperature and the reflux temperature.

The threo alcohol of general formula (VIII) is then converted into the threo intermediate of general formula (II) in which $R_1$ represents a methyl group, in two steps: the alcohol function is first converted into an electrophilic group, for example a methanesulfonate group, via the action of methanesulfonyl chloride, in a chlorinated solvent such as dichloromethane, and in the presence of a base such as triethylamine, between 0° C. and room temperature, and the electrophilic group is then reacted with liquefied ammonia at −50° C., in an alcohol such as ethanol, in a closed medium such as an autoclave, between −50° C. and room temperature.

The carbamate of general formula (VII) may also be deprotected using a strong base such as aqueous potassium hydroxide, in an alcohol such as methanol, to give the threo amino alcohol of general formula (IX), followed by an N-alkylation using a halogenated derivative of formula $R_1Z$, in which $R_1$ is as defined above, but other than a hydrogen atom, and Z represents a halogen atom, in the presence of a base such as potassium carbonate, in a polar solvent such as N,N-dimethylformamide, between room temperature and 100° C. The alcohol of general formula (X) thus obtained is then treated as described with respect to the alcohol of general formula (VIII).

Another process variant, illustrated by Scheme 3 below, may be used when $R_1$ represents a methyl group and X represents a hydrogen atom. The pyridine oxime of formula (XI) is quaternized, for example via the action of methyl trifluoromethanesulfonate, in an ether solvent such as diethyl ether, at room temperature. The pyridinium salt thus obtained, of formula (XII), is then subjected to a hydrogenation under a hydrogen atmosphere, in the presence of a catalyst such as platinum oxide, in a mixture of alcohol and of aqueous acid such as ethanol and 1N hydrochloric acid. The diamine of general formula (II) in which $R_1$ represents a methyl group and X represents a hydrogen atom is obtained in the form of a 9/1 threo/erythro mixture of the two diastereoisomers. It can be salified, for example with oxalic acid, and then purified by recrystallization of the oxalate formed from a mixture of alcohol and of an ether solvent such as methanol and diethyl ether, to give the pure threo diastereoisomer (1R,2R;1S,2S).

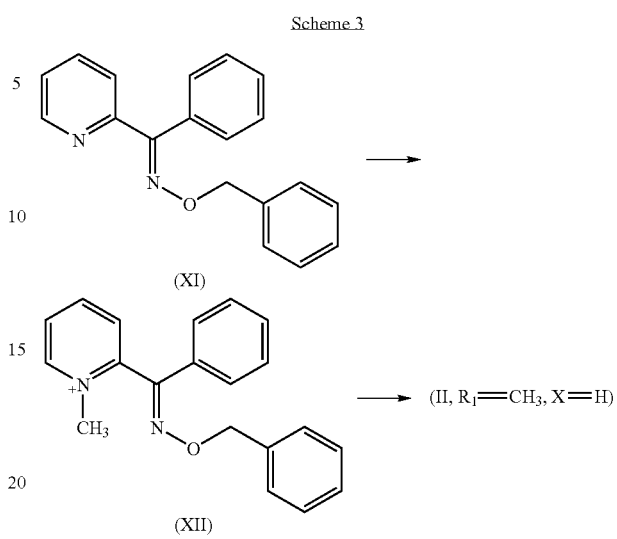

Scheme 3

The compounds of general formula (II) in which $R_1$ represents a hydrogen atom may be prepared according to Scheme 2, with use of a compound of general formula (I) in which $R_1$ represents an optionally substituted phenylmethyl group, followed by deprotection of the nitrogen of the piperidine ring, for example with an oxidizing agent or with a Lewis acid, such as boron tribromide, or via hydrogenolysis, i.e. an alkenyl group, preferably an allyl group, and in deprotecting the nitrogen with a $Pd^0$ complex, to obtain a compound of general formula (I) in which $R_1$ represents a hydrogen atom.

Moreover, the chiral compounds of general formula (I) corresponding to the (1R,2R) or (1S,2S) enantiomers of the threo diastereoisomer may also be obtained by separation of the racemic compounds by high-performance liquid chromatography (HPLC) on a chiral column, or by resolution of the racemic amine of general formula (II) by using a chiral acid such as tartaric acid, camphorsulfonic acid, dibenzoyltartaric acid or N-acetyl leucine, by fractional and preferential recrystallization of a diastereoisomeric salt, in a solvent of alcohol type, or alternatively via enantioselective synthesis according to Scheme 2 with use of a chiral Weinreb amide of formula (IV).

The racemic or chiral Weinreb amide of formula (IV), and also the ketone of general formula (VI), may be prepared according to a method similar to that described in Eur. J. Med. Chem., 35, (2000), 979-988 and J. Med. Chem., 41, (1998), 591-601. The phenyllithium compound of general formula (V), in which X represents a hydrogen atom, is commercially available. Its substituted derivatives may be prepared according to a method similar to that described in Tetrahedron Lett., 57, 33, (1996), 5905-5908. The pyridine oxime of general formula (XI) may be prepared according to a method similar to that described in patent application EP-0 366 006. The amine of general formula (IX) in which X represents a hydrogen atom may be prepared in the chiral series according to a method described in patent U.S. Pat. No. 2,928,835. Finally, the amine of general formula (XIII) may be prepared according to a method similar to that described in Chem. Pharm. Bull., 32, 12, (1984), 4893-4906 and Synthesis, (1976), 593-595.

The acids and acid chlorides of general formula (III) are commercially available, except for 4-[2-chloro-3-(trifluoromethyl)phenyl]-1H-imidazole-2-carboxylic acid, which may be prepared under conditions comparable to those described in patent application EP-0 365 030 and in patent U.S. Pat. No. 3,336,300.

The examples that follow illustrate the preparation of a number of compounds of the invention. The elemental microanalyses, the IR and NMR spectra and the HPLC on a chiral column confirm the structures and the enantiomeric purities of the compounds obtained.

The numbers given in parentheses in the titles of the examples correspond to those in the first column of the table given later.

Example 1

Compound 4

Threo-2,5-dichloro-N-[(1-methyl-2-piperidyl)(phenyl)methyl]-3-thiophenecarboxamide hydrochloride 1:1

1.1.
2-(Benzyloxyiminophenylmethyl)-1-methylpyridinium trifluoromethanesulfonate To a suspension of 35 g (120 mmol) of phenyl(2-pyridyl)methanone O-benzyl oxime in 200 ml of diethyl ether are added dropwise, at 0° C., 17.4 ml (120 mmol) of methyl trifluoromethanesulfonate and the mixture is stirred at room temperature for 3 hours. The precipitate formed is collected by filtration and dried under reduced pressure.

49 g of product are obtained, which product is used without further purification in the following step.

1.2.
Threo-(1-methylpiperidin-2-yl)phenylmethanamine ethanedioate 1:2

14.8 g (31.89 mmol) of 2-(benzyloxyiminophenylmethyl)-1-methylpyridinium trifluoromethanesulfonate and 0.74 g of platinum oxide are placed in 50 ml of ethanol and 50 ml of 1N hydrochloric acid in a Parr flask, and hydrogenation is performed for 5 hours.

The ethanol is evaporated off under reduced pressure, the residue is extracted with dichloromethane, the aqueous phase is separated out, aqueous ammonia solution is added thereto and the mixture is extracted with dichloromethane. After washing the combined organic phases, drying over sodium sulfate, filtering and evaporating off the solvent under reduced pressure, 6.7 g of oily product comprising 10% of erythro diastereoisomer are obtained.

The ethanedioate is prepared by dissolving these 6.7 g of base in methanol, via the action of two equivalents of ethanedioic acid dissolved in a minimum amount of methanol.

The salt obtained is purified by recrystallization from a mixture of methanol and diethyl ether.

4.7 g of ethanedioate of the pure threo diastereoisomer are finally isolated.

Melting point: 156-159° C.

1.3. Threo-2,5-dichloro-N-(1-methyl-2-piperidyl)(phenyl)methyl]thiophene-3-carboxamide hydrochloride 1:1

0.768 g (4 mmol) of 2,5-dichlorothiophene-3-carboxylic acid dissolved in 15 ml of dichloromethane is introduced into a 100 ml round-bottomed flask, 0.651 ml (4.7 mmol) of triethylamine and 0.447 ml (4.7 mmol) of ethyl chloroformate are then added and the reaction mixture is stirred at room temperature for 2 hours.

0.80 g (3.9 mmol) of threo-(1-methyl-2-piperidyl)phenylmethanamine dissolved in 15 ml of dichloromethane is added and stirring is continued at room temperature for 12 hours.

The mixture is treated with water and extracted several times with dichloromethane. After washing the organic phases with water and then with aqueous 1N sodium hydroxide solution, drying over sodium sulfate, filtering and evaporating off the solvent under reduced pressure, the residue is purified by column chromatography on silica gel, eluting with a 97/3 to 95/5 mixture of dichloromethane and methanol.

0.6 g of oily product is obtained, the hydrochloride of which is prepared by adding a 0.1N solution of hydrogen chloride in 2-propanol.

After evaporating off the solvents under reduced pressure, the white solid obtained is recrystallized from a mixture of isopropyl ether and 2-propanol.

0.474 g of hydrochloride is finally isolated in the form of a white solid.

Melting point: 216-217° C.

Example 2

Compound 5

2,5-Dichloro-N-[(S)-[(2S)-1-methyl-2-piperidyl](phenyl)methyl]thiophene-3-carboxamide hydrochloride 1:1

2.1. 1,1-dimethylethyl(2S)-2-benzoylpiperidine-1-carboxylate 11.8 g (43.3 mmol) of 1,1-dimethylethyl(2S)-2-(N-methoxy-N-methylcarbamoyl)piperidine-1-carboxylate are introduced into 100 ml of anhydrous diethyl ether in a 500 ml round-bottomed flask, under a nitrogen atmosphere, the medium is cooled to −23° C., 21.6 ml (43.2 mmol) of a 1.8M solution of phenyllithium in a 70/30 mixture of cyclohexane and diethyl ether are added dropwise and the mixture is stirred at room temperature for 3 hours. After hydrolysis with saturated aqueous sodium chloride solution, the aqueous phase is separated out and extracted with ethyl acetate. The organic phase is dried over sodium sulfate, filtered and concentrated under reduced pressure, and the residue is purified by column chromatography on silica gel, eluting with a mixture of ethyl acetate and cyclohexane.

4.55 g of solid product are obtained.

Melting point: 123-125° C.

$[\alpha]^{25}_D$=−25.4° (c=2.22; $CH_2Cl_2$) ee=97.2%.

2.2. 1,1-Dimethylethyl(1S)-2-[(2S)-hydroxy(phenyl)methyl]piperidine-1-carboxylate 4.68 g (16.2 mmol) of 1,1-dimethylethyl(2S)-2-benzoylpiperidine-1-carboxylate are introduced into 170 ml of anhydrous tetrahydrofuran in a 500 ml round-bottomed flask, under a nitrogen atmosphere, the solution is cooled to −78° C., 48.5 ml (48.5 mmol) of a 1M solution of L-Selectride® (lithium tri-sec-butylborohydride) in tetrahydrofuran are added dropwise and the mixture is stirred at room temperature for 5 hours.

The resulting mixture is hydrolyzed slowly under cold conditions with 34 ml of water and 34 ml of aqueous 35% hydrogen peroxide solution, and the mixture is allowed to warm to room temperature while stirring over 2 hours.

The resulting mixture is diluted with water and ethyl acetate, and the aqueous phase is separated out and extracted with ethyl acetate. After washing the combined organic phases, drying over sodium sulfate, filtering and evaporating, the residue is purified by column chromatography on silica gel, eluting with a mixture of ethyl acetate and cyclohexane.

4.49 g of a pale yellow oil are obtained.

$[\alpha]^{25}_D$=+63.75° (c=0.8; $CH_2Cl_2$) ee=97.8%.

2.3. (1S)-[(2S)-(1-methyl-2-piperidyl)]phenylmethanol 2.96 g (78.1 mmol) of lithium aluminum hydride are introduced into 50 ml of anhydrous tetrahydrofuran in a 200 ml two-necked flask, under a nitrogen atmosphere, the mixture is refluxed, 4.49 g (15.4 mmol) of a solution of 1,1-dimethylethyl(1S)-2-[(2S)-hydroxy(phenyl)methyl]piperidine-1-carboxylate in 35 ml of tetrahydrofuran are added and the mixture is maintained at reflux for 3.5 hours.

The mixture is cooled, hydrolyzed slowly with 0.1 M potassium sodium tartrate solution and stirred overnight. The resulting mixture is filtered, the precipitate is rinsed with tetrahydrofuran and the filtrate is then concentrated under reduced pressure.

2.95 g of a colorless oily product are obtained.

2.4. (1S)-[(2S)-(1-methyl-2-piperidyl)]phenylmethanamine 2.95 g (14.4 mmol) of (1S)-[(2S)-(1-methyl-2-piperidyl)]phenylmethanol and 2 ml (14.4 mmol) of triethylamine are introduced into 70 ml of anhydrous dichloromethane in a 250 ml round-bottomed flask, under a nitrogen atmosphere, the medium is cooled to 0° C., 1.1 ml (14.4 mmol) of methanesulfonyl chloride are added and the mixture is allowed to return slowly to room temperature over 2 hours and is concentrated under reduced pressure.

Liquefied ammonia is introduced into an autoclave equipped with a magnetic stirrer and cooled to −50° C., a solution of the methanesulfonate prepared above in 30 ml of absolute ethanol is added, and the autoclave is closed and stirred for 48 hours.

The mixture is transferred into a round-bottomed flask, the solvents are evaporated off under reduced pressure and the amine is isolated in the form of an oily product, which is used without further purification in the following step.

2.5. 2,5-Dichloro-N-[(1S)-[(2S)-1-methyl-2-piperidyl](phenyl)methyl]thiophene-3-carboxamide hydrochloride 1:1

0.37 g (1.88 mmol) of 2,5-dichlorothiophene-3-carboxylic acid is introduced into 15 ml of dichloromethane in a 250 ml round-bottomed flask, 0.31 ml (2.25 mmol) of triethylamine and 0.21 ml (2.25 mmol) of ethyl chloroformate are successively added and the mixture is stirred at room temperature for 1 hour.

0.38 g (1.88 mmol) of (1S)-[(2S)-(1-methyl-2-piperidyl)]phenylmethanamine dissolved in 10 ml of dichloromethane is added and stirring is continued at room temperature for 12 hours.

The mixture is treated with water and extracted several times with dichloromethane, the organic phases are combined, washed with aqueous 1N sodium hydroxide solution, dried over sodium sulfate and filtered, and the filtrate is concentrated under reduced pressure.

The crude residue is purified by column chromatography on silica gel, eluting with a 98/2 mixture of dichloromethane and methanol containing 0.1% aqueous ammonia. 0.368 g of oily product is obtained, the hydrochloride of which is prepared by addition of a 0.1N solution of hydrogen chloride in 2-propanol.

After evaporating off the solvent under reduced pressure, the solid is recrystallized from a mixture of 2-propanol and isopropyl ether.

0.36 g of hydrochloride is finally isolated in the form of a pale yellow solid.

Melting point: 134-136° C.

$[\alpha]^{25}_D$=+45.6 (c=0.99); $CH_3OH$.

Example 3

Compound 18

Threo-4-[2-chloro-3-(trifluoromethyl)phenyl]-N-[(1-methyl-2-piperidyl)(phenyl)methyl]-1H-imidazole-2-carboxamide hydrochloride 1:1

0.1 g (0.344 mmol) of 4-(2-chloro-3-(trifluoromethyl)phenyl]-1H-imidazole-2-carboxylic acid, 0.066 g (0.344 mmol) of 1-[3-(dimethylamino)propyl]-3-ethyl-carbodiimide, and 0.047 g (0.344 mmol) of 1-hydroxybenzotriazole dissolved in 10 ml of dichloromethane are introduced into a 50 ml round-bottomed flask and the mixture is stirred at room temperature for 5 minutes.

0.072 g (0.344 mmol) of threo-(1-methyl-2-piperidyl)phenylmethanamine (prepared according to Example 1.2) is added to a few ml of dichloromethane and stirring is continued for 6 hours.

The mixture is treated with water and extracted several times with dichloromethane, the organic phases are washed with water and then with aqueous 1N sodium hydroxide solution, then with saturated aqueous sodium chloride solution and dried over sodium sulfate, and the solvent is evaporated off under reduced pressure. The residue is purified by column chromatography on silica gel, eluting with a mixture of dichloromethane and methanol.

91 mg of product is obtained, the hydrochloride of which is prepared by adding a 0.1N solution of hydrogen chloride in 2-propanol. The solvent is partially evaporated off under reduced pressure to obtain, after crystallization, 104 mg of solid white compound.

Melting point: 188-195° C.

The table on the following page illustrates the chemical structures and the physical properties of a number of compounds according to the invention.

In the "Salt" column; "-" denotes a compound in base form and "HCl" denotes a hydrochloride.

The optical rotation of compound 5 is $[\alpha]^{25}_D$=+45.6° (c=0.99); $CH_3OH$.

TABLE
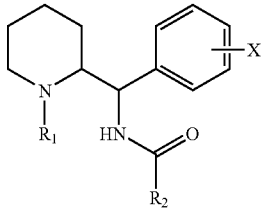
| No. | Stereochemistry | R₁ | X | R₂ | Salt | F(° C.) |
|---|---|---|---|---|---|---|
| 1 | threo (1R,2R;1S,2S) | CH₃ | H | 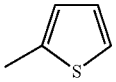 | — | M + H = 315 |
| 2 | threo (1R,2R;1S,2S) | CH₃ | H | 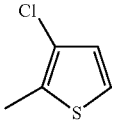 | HCl | 211-212 |
| 3 | threo (1R,2R;1S,2S) | CH₃ | H | 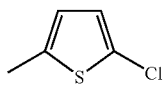 | — | 122-125 |
| 4 | threo (1R,2R;1S,2S) | CH₃ | H | 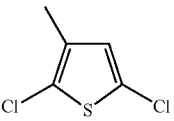 | HCl | 216-217 |
| 5 | threo (1S,2S) | CH₃ | H | 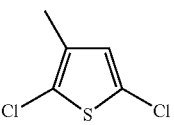 | HCl | 134-136 |
| 6 | threo (1R,2R;1S,2S) | CH₃ | H | 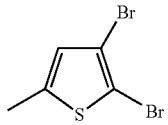 | — | 134-136 |
| 7 | threo (1R,2R;1S,2S) | CH₃ | H | 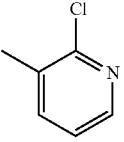 | — | 154-156 |
| 8 | threo (1R,2R;1S,2S) | CH₃ | H | 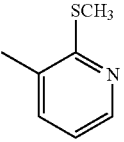 | — | 152-155 |
| 9 | threo (1R,2R;1S,2S) | CH₃ | H | 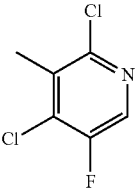 | HCl | 219-221 |

TABLE-continued

| No. | Stereochemistry | R₁ | X | R₂ | Salt | F(° C.) |
|-----|-----------------|-----|---|-----|------|---------|
| 10 | threo (1R,2R;1S,2S) | CH₃ | H | 3-chloro-2-methylbenzo[b]thiophene | — | 66-74 |
| 11 | threo (1R,2R;1S,2S) | CH₃ | H | 6-methyl-1H-indole | — | 99-100 |
| 12 | threo (1R,2R;1S,2S) | CH₃ | H | 5-methyl-1H-indole | HCl | 214-215 |
| 13 | threo (1R,2R;1S,2S) | CH₃ | H | 2,5-dimethyl-1H-benzimidazole | HCl | M + H = 363 |
| 14 | threo (1R,2R;1S,2S) | CH₃ | H | 5-methyl-1H-benzotriazole | — | 60-61 |
| 15 | threo (1R,2R;1S,2S) | CH₃ | H | 1-bromo-2-methylnaphthalene | HCl | 273-274 |
| 16 | threo (1R,2R;1S,2S) | CH₃ | H | 7-chloro-3,8-dimethylquinoline | — | 236-237 |
| 17 | threo (1R,2R;1S,2S) | CH₃ | H | 3,7-dichloro-8-methylquinoline | — | 268-269 |
| 18 | threo (1R,2R;1S,2S) | CH₃ | H | 4-[2-chloro-3-(trifluoromethyl)phenyl]-2-methyl-1H-imidazole | HCl | 188-195 |

The compounds of the invention were subjected to a series of pharmacological tests that demonstrated their value as therapeutically active substances.

Study of Glycine Transportation in SK-N-MC Cells Expressing the Native Human Transporter glyt1

The uptake of [$^{14}$C]glycine is studied in SK-N-MC cells (human neuroepithelial cells) expressing the native human transporter glyt1 by measuring the radioactivity incorporated in the presence or absence of the test compound. The cells are cultured as a monolayer for 48 hours in plates pretreated with 0.02% fibronectin. On the day of the experiment, the culture medium is removed and the cells are washed with Krebs-HEPES buffer ([4-(2-hydroxyethyl)-1-piperazine]ethanesulfonic acid) at pH 7.4. After preincubation for 10 minutes at 37° C. in the presence either of buffer (control batch) or of test compound at various concentrations or of 10 mM of glycine (determination of the nonspecific uptake), 10 μM of [$^{14}$C] glycine (specific activity 112 mCi/mmol) are then added. Incubation is continued for 10 minutes at 37° C., and the reaction is quenched by washing twice with pH 7.4 Krebs-HEPES buffer. The radioactivity incorporated by the cells is then estimated after adding 100 μl of liquid scintillant and stirring for 1 hour. Counting is performed on a Microbeta Tri-Lux™ counter. The efficacy of the compound is determined by means of the $IC_{50}$, which is the concentration of compound that reduces by 50% the specific uptake of glycine, defined by the difference in radioactivity incorporated by the control batch and the batch that received 10 mM of glycine.

The compounds of the invention have an $IC_{50}$ in this test of about from 0.01 to 10 μM.

Study of the Glycine Transportation in Mouse Spinal Cord Homogenate

The uptake of [$^{14}$C]glycine by the transporter glyt2 is studied in mouse spinal cord homogenate by measuring the radioactivity incorporated in the presence or absence of test compound.

After euthanizing the animals (male OF1 Iffa Credo mice weighing 20 to 25 g on the day of the experiment), the spinal cord of each animal is rapidly removed, weighed and stored on ice. The samples are homogenized in pH 7.4 Krebs-HEPES buffer ([4-(2-hydroxyethyl)-1-piperazine]ethanesulfonic acid), in a proportion of 25 ml/g of tissue.

50 μl of homogenate are preincubated for 10 minutes at 25° C. in the presence of pH 7.4 Krebs-HEPES buffer and of test compound at various concentrations, or of 10 mM of glycine to determine the nonspecific uptake. [$^{14}$C]glycine (specific activity=112 mCi/mmol) is then added over 10 minutes at 25° C. to a final concentration of 10 μM. The reaction is quenched by vacuum filtration and the radioactivity is estimated by solid scintillation by counting on a Microbeta Tri-Lux™ counter. The efficacy of the compound is determined by means of the $IC_{50}$, the concentration capable of reducing by 50% the specific uptake of glycine, defined by the difference in radioactivity incorporated by the control batch and the batch that received 10 mM of glycine.

The compounds of the invention have an $IC_{50}$ in this test of about from 0.1 to 10 μM.

These results suggest that the compounds of the invention may be used for treating behavioral disorders associated with dementia, psychoses, in particular schizophrenia (deficient form and productive form) and acute or chronic extrapyramidal symptoms induced by neuroleptics, for the treatment of various forms of anxiety, panic attacks, phobias, compulsive obsessive disorders, for treating various forms of depression, including psychotic depression, for treating disorders caused by alcohol abuse or weaning from alcohol, sexual behavior disorders, eating disorders and for treating migraine.

Moreover, the compounds of the invention may be used for treating painful muscle contracture in rheumatology and in acute spinal pathology, for treating spastic contractures of medullary or cerebral origin, for the symptomatic treatment of acute and subacute pain of light to moderate intensity, for treating intense and/or chronic pain, neurogenic pain and intractable pain, for treating Parkinson's disease and Parkinson-like symptoms of neurodegenerative origin or induced by neuroleptics, for treating partial primary and secondary generalized epilepsy of simple or complex symptomology, mixed forms and other epileptic syndromes in addition to another antiepileptic treatment, or in monotherapy, for the treatment of sleep apnea, and for neuroprotection.

Accordingly, a subject of the present invention is also pharmaceutical compositions containing an effective dose of at least one compound according to the invention, in the form of base or of pharmaceutically acceptable salt or solvate, and as a mixture, where appropriate, with suitable excipients.

Said excipients are chosen according to the pharmaceutical form and the desired mode of administration.

The pharmaceutical compositions according to the invention may thus be intended for oral, sublingual, subcutaneous, intramuscular, intravenous, topical, intra-tracheal, intranasal, transdermal, rectal or intraocular administration.

The unit administration forms may be, for example, tablets, gel capsules, granules, powders, oral or injectable solutions or suspensions, transdermal patches or suppositories. Pomades, lotions and eyedrops may be envisioned for topical administration.

Said unit forms are dosed to allow a daily administration of from 0.01 to 20 mg of active principle per kg of body weight, according to the galenical form.

To prepare tablets, a pharmaceutical vehicle, which may be composed of diluents, for instance lactose, microcrystalline cellulose or starch, and formulating adjuvants, for instance binders (polyvinylpyrrolidone, hydroxypropylmethylcellulose, etc.), glidants, for instance silica, and lubricants, for instance magnesium stearate, stearic acid, glyceryl tribehenate or sodium stearyl fumarate, are added to the micronized or nonmicronized active principle. Wetting agents or surfactants such as sodium lauryl sulfate may also be added.

The preparation techniques may be direct tableting, dry granulation, wet granulation or hot melting.

The tablets may be plain, sugar-coated, for example coated with sucrose, or coated with various polymers or other suitable materials. They may be designed to allow rapid, delayed or sustained release of the active principle by means of polymer matrices or specific polymers used in the coating.

To prepare gel capsules, the active principle is mixed with dry pharmaceutical vehicles (simple mixing, dry or wet granulation, or hot melting), or liquid or semisolid pharmaceutical vehicles.

The gel capsules may be hard or soft, with or without a film coating, so as to have rapid, sustained or delayed activity (for example for an enteric form).

A composition in the form of a syrup or elixir or for administration in the form of drops may contain the active principle together with a sweetener, preferably a calorie-free sweetener, methylparaben or propylparaben as antiseptic, a flavoring and a dye.

The water-dispersible powders and granules may contain the active principle as a mixture with dispersants or wetting agents, or dispersants such as polyvinylpyrrolidone, and also with sweeteners and flavor enhancers.

For rectal administration, use is made of suppositories prepared with binders that melt at the rectal temperature, for example cocoa butter or polyethylene glycols.

Aqueous suspensions, isotonic saline solutions or injectable sterile solutions containing pharmacologically compatible dispersants and/or wetting agents, for example propylene glycol or butylene glycol, are used for parenteral administration.

The active principle may also be formulated in the form of microcapsules, optionally with one or more supports or additives, or alternatively with a polymer matrix or with a cyclodextrin (transdermal patches, sustained-released forms).

The topical compositions according to the invention comprise a medium that is compatible with the skin. They may especially be in the form of aqueous, alcoholic or aqueous-alcoholic solutions, gels, water-in-oil or oil-in-water emulsions having the appearance of a cream or a gel, microemulsions or aerosols, or alternatively in the form of vesicular dispersions containing ionic and/or nonionic lipids. These galenical forms are prepared according to the usual methods of the fields under consideration.

Finally, the pharmaceutical compositions according to the invention may contain, along with a compound of general formula (I), other active principles that may be useful in the treatment of the disorders and diseases indicated above.

The invention claimed is:

1. A compound of formula (I)

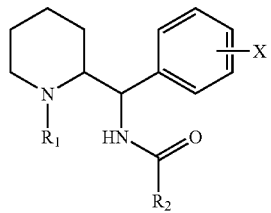

in which $R_1$ represents either a hydrogen atom or a linear or branched $(C_1-C_7)$alkyl group optionally substituted with one or more fluorine atoms, or a $(C_3-C_7)$cycloalkyl group, or a $(C_3-C_7)$cycloalkyl $(C_1-C_3)$alkyl group, or a phenyl$(C_1-C_3)$alkyl group optionally substituted with one or two methoxy groups, or a $(C_2-C_4)$alkenyl group, or a $(C_2-C_4)$alkynyl group, X represents a hydrogen atom or one or more substituents chosen from halogen atoms and trifluoromethyl and linear or branched $(C_1-C_4)$alkyl and $(C_1-C_4)$alkoxy groups, $R_2$ represents a group chosen from thienyl, and benzothienyl, and optionally substituted with one or more substituents chosen from halogen atoms and $(C_1-C_4)$alkyl, $(C_1-C_4)$alkoxy, thio$(C_1-C_4)$alkyl or phenyl groups optionally substituted with one or more substituents chosen from halogen atoms and trifluoromethyl, $(C_1-C_4)$alkyl and $(C_1-C_4)$alkoxy groups, in the form of free base or of acid-addition salt.

2. A compound according to claim 1 selected from the group consisting of:

threo-2,5-dichloro-N-[(1-methyl-2-piperidyl)(phenyl)methyl]thiophene-3-carboxamide; and 2,5-dichloro-N-[(S)-[(2S)-1-methyl-2-piperidyl](phenyl)methyl]thiophene-3-carboxamide;

or an acid addition salt thereof.

3. A pharmaceutical composition which comprises a compound as claimed in claim 1, or a pharmaceutically acceptable salt thereof, combined with an excipient.

4. A method for treating a behavioral disorder selected from the group consisting of schizophrenia, anxiety, and depression, which comprises administering to a patient with said disorder an effective amount of a compound according to claim 1, or a pharmaceutically acceptable salt thereof.

* * * * *